United States Patent
Ikuma et al.

(10) Patent No.: US 8,894,566 B2
(45) Date of Patent: Nov. 25, 2014

(54) ENDOSCOPE SYSTEM

(71) Applicant: Olympus Medical Systems Corp., Tokyo (JP)

(72) Inventors: Soichi Ikuma, Hachioji (JP); Junichi Onishi, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 14/087,450

(22) Filed: Nov. 22, 2013

(65) Prior Publication Data
US 2014/0088357 A1 Mar. 27, 2014

Related U.S. Application Data

(63) Continuation of application No. PCT/JP2013/050381, filed on Jan. 11, 2013.

(30) Foreign Application Priority Data

Mar. 6, 2012 (JP) .................................. 2012-049467

(51) Int. Cl.
*A61B 1/00* (2006.01)
*A61B 1/04* (2006.01)
(Continued)

(52) U.S. Cl.
CPC ............... *A61B 1/00009* (2013.01); *A61B 1/04* (2013.01); *A61B 6/463* (2013.01); *A61B 6/12*
(Continued)

(58) Field of Classification Search
CPC ........... A61B 19/5225; A61B 19/5244; A61B 19/5253; A61B 19/5257; A61B 19/5265; A61B 19/562; A61B 19/564; A61B 19/566; A61B 19/568; A61B 2019/501; A61B 5019/505; A61B 2019/507; A61B 2019/508; A61B 2019/5238; A61B 2019/524; A61B 2019/5242
USPC ......... 600/117, 118, 109, 110, 103, 139, 145, 600/146
See application file for complete search history.

(56) References Cited

U.S. PATENT DOCUMENTS

2005/0020878 A1* 1/2005 Ohnishi et al. ................ 600/117
2005/0182295 A1* 8/2005 Soper et al. ................... 600/117
(Continued)

FOREIGN PATENT DOCUMENTS

EP 2 422 684 A1 2/2012
JP 2002-200030 A 7/2002
(Continued)

OTHER PUBLICATIONS

International Search Report dated Feb. 12, 2013 issued in PCT/JP2013/050381.

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

An endoscope system includes: an image processing portion that constructs three-dimensional data based on preoperative multi-slice image data and extracts a predetermined luminal organ; a position detection apparatus that acquires position information of an image pickup portion; a position alignment portion that makes position information of the image pickup portion correspond to coordinates of the three-dimensional data; and an image processing portion that generates trail information based on the position information of the image pickup portion, and based on a result of the position alignment portion, creates an image in which past trail information, insertion shape information including current distal end position information with respect to the image pickup portion, and determination information obtained by determining whether or not the image pickup portion passes through a duct in three-dimensional data of the predetermined luminal organ are superimposed in a distinguishable manner on three-dimensional image information of the predetermined luminal organ.

8 Claims, 14 Drawing Sheets

(51) Int. Cl.
*A61B 6/12* (2006.01)
*A61B 6/00* (2006.01)
*A61B 19/00* (2006.01)
*G02B 23/24* (2006.01)

(52) U.S. Cl.
CPC . (2013.01); *A61B 2019/5238* (2013.01); *A61B 6/547* (2013.01); *A61B 19/5244* (2013.01); *G02B 23/2415* (2013.01); *A61B 1/0005* (2013.01)
USPC ............................ 600/117; 600/103; 600/109

(56) References Cited

U.S. PATENT DOCUMENTS

2006/0293565 A1* 12/2006 Uchimura et al. ............ 600/156
2007/0013710 A1* 1/2007 Higgins et al. ................ 345/581
2007/0061726 A1* 3/2007 Rahn et al. .................... 715/719
2007/0276234 A1* 11/2007 Shahidi ......................... 600/437
2008/0071140 A1* 3/2008 Gattani et al. ................ 600/117
2010/0030063 A1* 2/2010 Lee et al. ...................... 600/424
2010/0121151 A1* 5/2010 Donhowe et al. ............. 600/141
2011/0224490 A1 9/2011 Kimura et al.

FOREIGN PATENT DOCUMENTS

| JP | 2005-312770 A | 11/2005 |
| JP | 2009-056239 A | 3/2009 |
| JP | 2009-279251 A | 12/2009 |
| JP | 4810622 B2 | 8/2011 |
| JP | 2012-024518 A | 2/2012 |
| WO | WO 2010/122823 A1 | 10/2010 |
| WO | WO 2012/014438 A1 | 2/2012 |

* cited by examiner

FIG.3

| TIME STAMP | COORDINATES IN REAL SPACE (POSITION DATA) | | | COORDINATES IN THREE-DIMENSIONAL DATA (POSITION DATA) | | | RESET |
|---|---|---|---|---|---|---|---|
| | X | Y | Z | X | Y | Z | |
| TS1 | A1 | B1 | C1 | D1 | E1 | F1 | ○ |
| TS2 | A2 | B2 | C2 | D2 | E2 | F2 | ○ |
| TS3 | A3 | B3 | C3 | D3 | E3 | F3 | ○ |
| TS4 | A4 | B4 | C4 | D4 | E4 | F1 | ○ |
| TS5 | A5 | B5 | C5 | D5 | E5 | F5 | — |
| ... | ... | ... | ... | ... | ... | ... | ... |
| TSn | An | Bn | Cn | Dn | En | Fn | — |

ENDOSCOPE SYSTEM

CROSS REFERENCE TO RELATED APPLICATION

This application is a continuation application of PCT/JP2013/050381 filed on Jan. 11, 2013 and claims benefit of Japanese Application No. 2012-049467 filed in Japan on Mar. 6, 2012, the entire contents of which are incorporated herein by this reference.

BACKGROUND OF THE INVENTION

1. Field of the Invention

The present invention relates to an endoscope system, and more particularly to an endoscope system that displays whether or not observation by means of an image pickup portion was performed in a superimposed manner on three-dimensional image information.

2. Description of the Related Art

Endoscope apparatuses are in widespread use as medical endoscopes that observe an organ inside a body cavity and, where necessary, perform therapeutic treatment using a treatment instrument. When performing observation or therapeutic treatment using such kind of endoscope apparatus, it is necessary to insert an insertion portion of an endoscope into a lumen, and quickly and accurately cause a distal end portion of the insertion portion to reach a destination such as a lesion part.

As navigation technology that causes an insertion portion of an endoscope to reach a destination, for example, Japanese Patent Application Laid-Open Publication No. 2002-200030 discloses an endoscope position detection apparatus that supports insertion of an insertion portion of an endoscope into a duct such as a bronchial tube.

In the case of renal calculi, the inside of the renal pelvis and renal calices is observed with an endoscope, and treatment is performed to remove the calculi by means of a treatment instrument that protrudes from the distal end of the endoscope. When carrying out such treatment using an endoscope in the renal pelvis and renal calices, X-ray photographing is performed during the treatment to ascertain the position of the endoscope as the endoscope passes through the renal pelvis and renal calices.

SUMMARY OF THE INVENTION

An endoscope system according to one aspect of the present invention includes: a storage portion that stores image information for constructing three-dimensional image information relating to a subject that is previously acquired; a luminal organ extraction portion that extracts a predetermined luminal organ by constructing the three-dimensional image information based on the image information; an image pickup portion that picks up an image of inside the subject; a position information acquisition portion that acquires position information of the image pickup portion; a position alignment portion that makes the position information acquired by the position information acquisition portion correspond to position information of three-dimensional image coordinates of the predetermined luminal organ; and an image processing portion that generates trail information based on the position information of the image pickup portion, and based on a result of the position alignment portion, creates an image in which past trail information in the trail information, insertion shape information including current distal end position information with respect to the image pickup portion, and determination information obtained by determining whether or not the image pickup portion passes through a duct in the predetermined luminal organ are superimposed in a distinguishable manner on three-dimensional image information of the predetermined luminal organ.

BRIEF DESCRIPTION OF THE DRAWINGS

FIG. 3 is a view that illustrates an example of position data that is stored in a distal end position storage portion;

FIG. 17 is a configuration diagram for describing the detailed configuration of an image processing apparatus 7a.

DETAILED DESCRIPTION OF THE PREFERRED EMBODIMENTS

Embodiments of the present invention are described in detail hereunder with reference to the drawings.

First Embodiment

Figure 1:
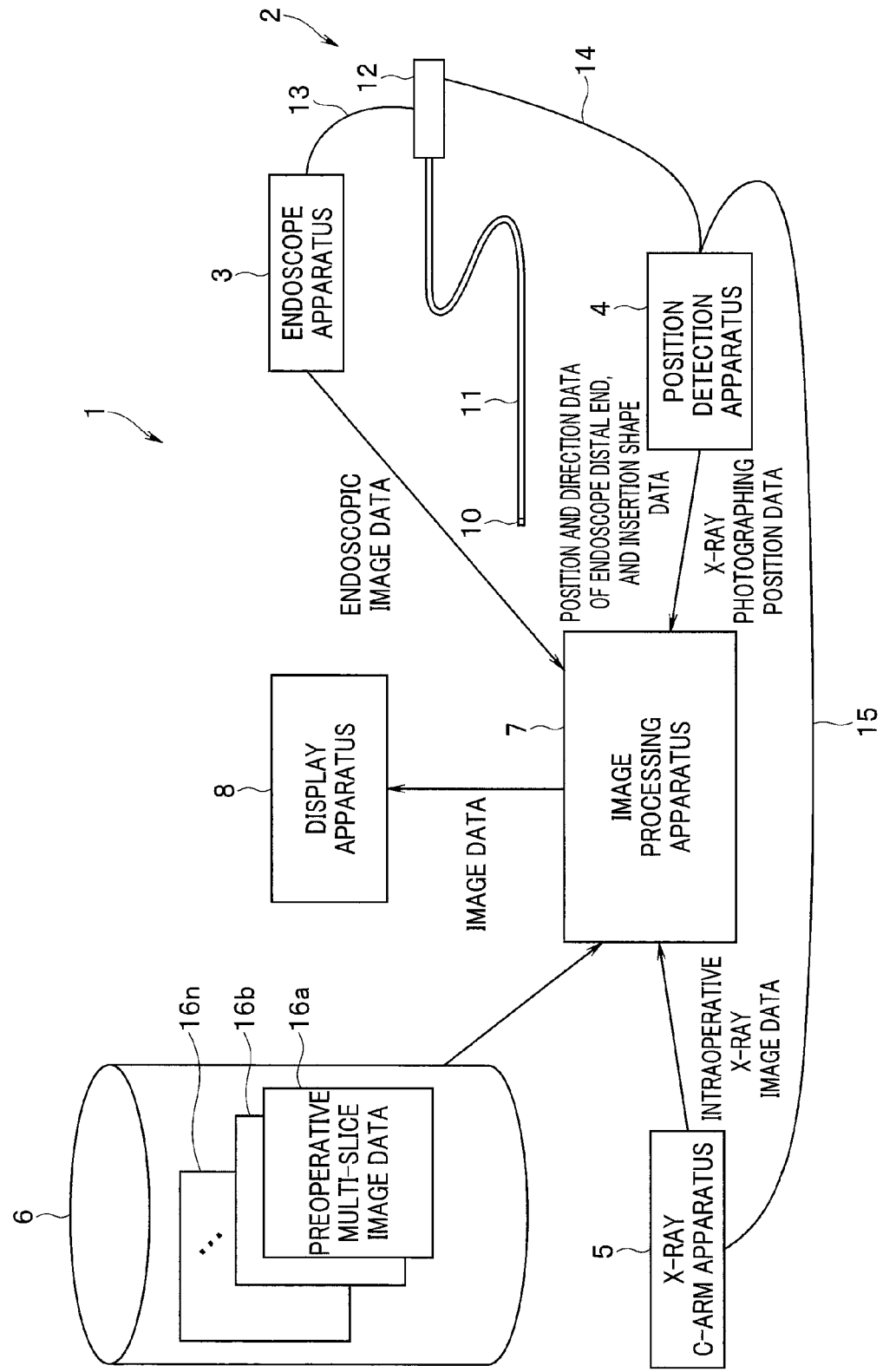
FIG. 1 is a configuration diagram illustrating a configuration of an endoscope system according to a first embodiment.

First, the configuration of an endoscope system according to a first embodiment of the present invention will be described based on FIG. 1. FIG. 1 is a configuration diagram that illustrates the configuration of an endoscope system according to the first embodiment.

As shown in FIG. 1, an endoscope system 1 includes an endoscope 2, an endoscope apparatus 3, a position detection apparatus 4, an X-ray C-arm apparatus 5, a server 6, an image processing apparatus 7, and a display apparatus 8.

The endoscope 2 includes an elongated insertion portion 11 having flexibility that is inserted into a subject, an operation portion 12 that is connected in series to a proximal end portion of the insertion portion 11, and a cable 13 that extends from a side face of the operation portion 12. An unshown connector is provided in a proximal end portion of the cable 13, and the endoscope 2 is connected through the connector to the endoscope apparatus 3.

A cable 14 and a cable 15 extend from the position detection apparatus 4. The position detection apparatus 4 is connected to the operation portion 12 of the endoscope 2 through an unshown connector provided in the proximal end portion of the cable 14, and is connected to the X-ray C-arm apparatus 5 through an unshown connector provided in the proximal end portion of the cable 15.

An image pickup device 10 such as a CCD that constitutes an image pickup portion is provided in the distal end portion of the insertion portion 11. The image pickup device 10 picks up an image of the inside of the subject. An image pickup signal of an image that is picked up by the image pickup device 10 is transmitted to the endoscope apparatus 3 through the operation portion 12 and the cable 13.

The endoscope apparatus 3 performs predetermined image processing on the image pickup signal transmitted thereto to thereby generate endoscopic image data. The generated endoscopic image data is taken in by the image processing apparatus 7.

In the insertion portion 11, a plurality of reception coils that are not shown in the drawings are provided at predetermined intervals from the distal end portion to the proximal end portion thereof. Each of the plurality of reception coils outputs an electrical signal in accordance with a magnetic field that the position detection apparatus 4 generates. The respective electrical signals that are outputted are transmitted to the position detection apparatus 4 through the operation portion 12 and the cable 14.

The position detection apparatus 4 as a position information acquisition portion performs calculations for detecting the position and direction of the distal end of the insertion portion 11 based on electrical signals from a reception coil that is provided in the distal end portion among the electrical signals from the plurality of reception coils, to thereby detect position and direction data of the distal end, more specifically, the image pickup portion of the insertion portion 11. The position detection apparatus 4 also performs calculations for detecting an insertion shape of the insertion portion 11 based on electrical signals from the plurality of reception coils to thereby detect insertion shape data of the insertion portion 11. The detected position and direction data of the distal end of the insertion portion 11 and insertion shape data of the insertion portion 11 are taken in by the image processing apparatus 7.

The X-ray C-arm apparatus 5 obtains intraoperative X-ray image data from multiple directions by rotating an X-ray C-arm that includes an X-ray generation portion and an X-ray detection portion at an arbitrary angle. The intraoperative X-ray image data is taken in by the image processing apparatus 7.

An unshown reception coil is also provided in the X-ray C-arm. The reception coil outputs an electrical signal in accordance with a magnetic field from the position detection apparatus 4. The outputted electrical signal is transmitted to the position detection apparatus 4 through the cable 15. The position detection apparatus 4 generates X-ray photographing position data by detecting the position of the X-ray C-arm and the like based on the transmitted electrical signal. The generated X-ray photographing position data is taken in by the image processing apparatus 7.

Preoperative multi-slice image data 16a to 16n such as, for example, CT or MRI image data is stored in the server 6. The preoperative multi-slice image data 16a to 16n is taken in by the image processing apparatus 7 via a LAN in a clinic, for example. Note that a configuration may also be adopted in which the preoperative multi-slice image data 16a to 16n is, for example, stored on a portable medium such as a CD-ROM and is taken in by the image processing apparatus 7 via the portable medium.

The image processing apparatus 7 performs predetermined image processing that is described later on the endoscopic image data from the endoscope apparatus 3, the position and direction data of the distal end of the insertion portion 11 from the position detection apparatus 4, the insertion shape data of the insertion portion 11, X-ray photographing position data, the X-ray image data from the X-ray C-arm apparatus 5, and the preoperative multi-slice image data 16a to 16n that is taken in from the server 6. The image processing apparatus 7 displays the obtained image data on the display apparatus 8.

Next, the detailed configuration of the image processing apparatus 7 and an image that is displayed on the display apparatus 8 will be described.

Figure 2:
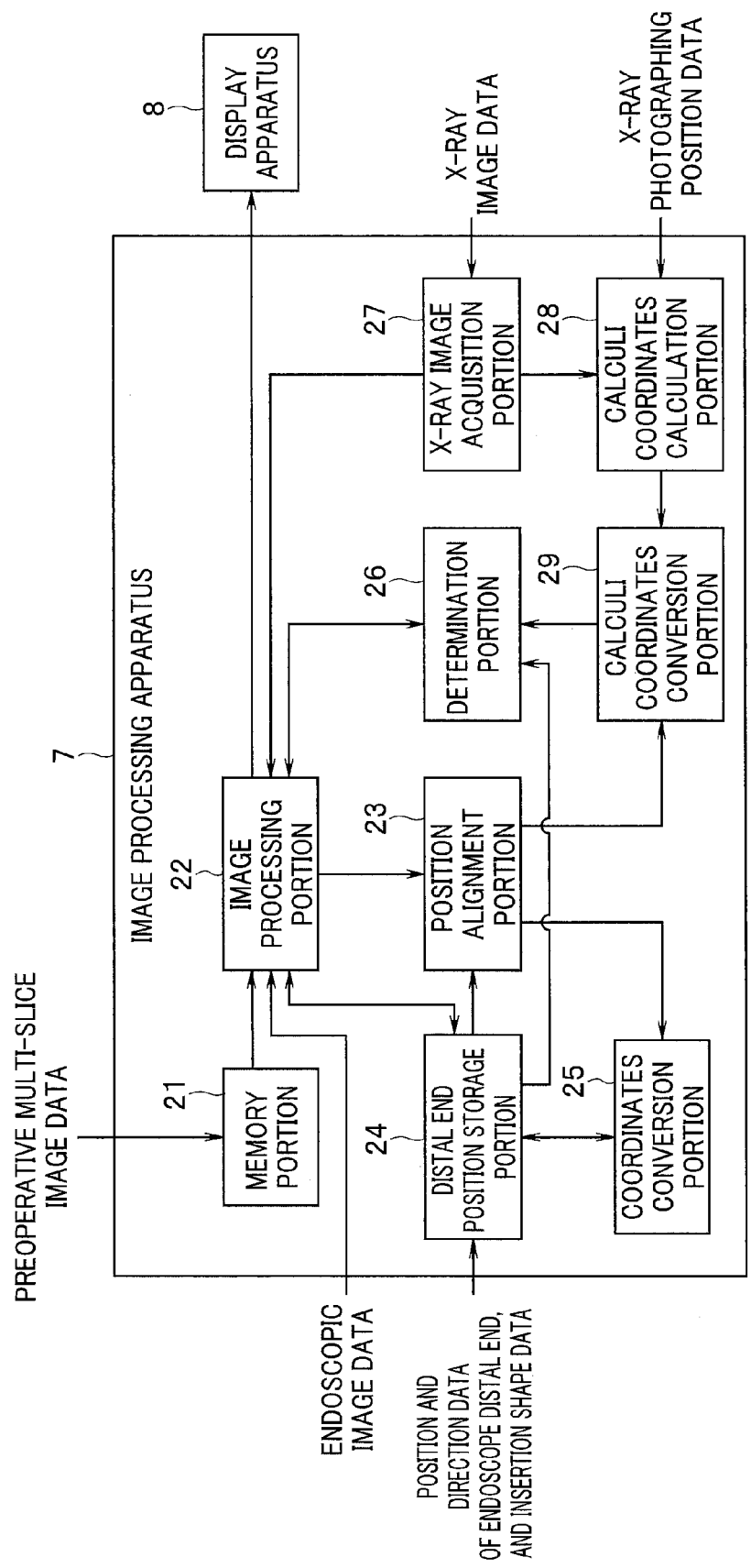
FIG. 2 is a configuration diagram for describing the detailed configuration of an image processing apparatus 7.
Figure 4:
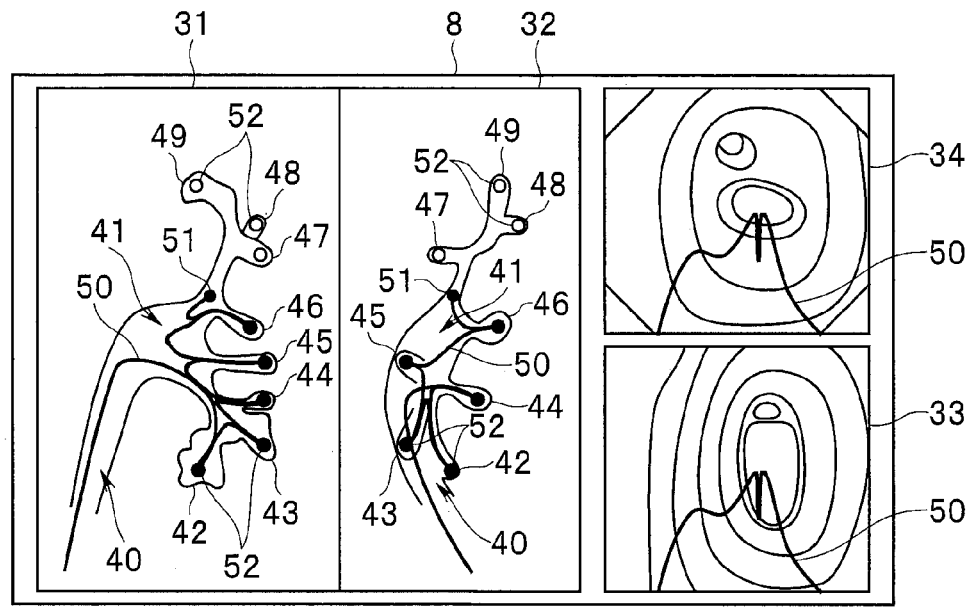
FIG. 4 is an explanatory view for describing an example of an image that is displayed on a display apparatus 8.

FIG. 2 is a configuration diagram for describing the detailed configuration of the image processing apparatus 7. FIG. 3 is a view that illustrates an example of position data that is stored in a distal end position storage portion. FIG. 4 is an explanatory view for describing an example of an image that is displayed on the display apparatus 8. FIG. 5 to FIG. 8 are explanatory views for describing other examples of an image that is displayed on the display apparatus 8.

Note that an image that is displayed on the display apparatus 8 that is shown in FIG. 4 is two-dimensional data that is subjected to image processing by an image processing portion 22 and is ultimately displayed on the display apparatus 8. Further, reference numerals of the two-dimensional data shown in FIG. 4 are used in the following description.

As shown in FIG. 2, the image processing apparatus 7 includes a memory portion 21, the image processing portion 22, a position alignment portion 23, a distal end position storage portion 24, a coordinates conversion portion 25, a determination portion 26, an X-ray image acquisition portion 27, a calculi coordinates calculation portion 28, and a calculi coordinates conversion portion 29.

The memory portion 21 as a storage portion stores the preoperative multi-slice image data 16a to 16n that is image information for constructing three-dimensional image information relating to the subject that is previously acquired from the server 6. The preoperative multi-slice image data 16a to 16n is read out by the image processing portion 22.

The image processing portion 22 that constitutes a luminal organ extraction portion constructs three-dimensional data 31 (see FIG. 4) based on the preoperative multi-slice image data 16a to 16n that is read out from the memory portion 21, extracts a predetermined luminal organ including a ureter 40, a renal pelvis 41, and renal calices 42 to 49, and outputs position coordinates thereof to the position alignment portion 23. Note that the image processing portion 22 may also be configured to construct three-dimensional data that includes not just the ureter 40, the renal pelvis 41, and the renal calices 42 to 49, but also includes the bladder and/or urethra. To enable observation of three-dimensional data from two directions, the image processing portion 22 generates three-dimensional data 32 in which the constructed three-dimensional data 31 is rotated at an arbitrary angle.

The image processing portion 22 that constitutes a virtual endoscopic image generation portion generates a virtual endoscopic image 33 which shows a predetermined luminal organ as viewed endoscopically from a predetermined observation point based on the three-dimensional data 31 or 32. The image processing portion 22 also performs predetermined image processing on endoscopic image data taken in from the endoscope apparatus 3 to generate an endoscopic image 34. The image processing portion 22 superimposes an insertion trail or the like of the distal end of the insertion portion 11 that is described later on the three-dimensional data 31 and 32, the virtual endoscopic image 33, and the endoscopic image 34 to create an image to be displayed on the display apparatus 8.

In addition, the image processing portion 22 extracts centerline data of the lumen in the constructed three-dimensional data 31, and also extracts coordinate values in the three-dimensional data of an end point of the centerline data. The image processing portion 22 outputs the coordinate values in the three-dimensional data of the centerline data to the position alignment portion 23, and outputs coordinate values in the three-dimensional data of the end point of the centerline data to the determination portion 26 as renal calices coordinates data of the renal calices 42 to 49.

As shown in FIG. 3, position and direction data with respect to real space of the distal end of the insertion portion 11 that was outputted from the position detection apparatus 4 is stored along with a time stamp TS in the distal end position storage portion 24. In the example in FIG. 3, only position data is listed, and A1, B1, and C1 as position data are associated with a time stamp TS1 and stored.

When an instruction to perform position alignment is received from a user, the position alignment portion 23 compares position data stored in the distal end position storage portion 24 and centerline data from the image processing portion 22, and calculates a conversion formula that converts real space coordinates to three-dimensional data coordinates.

The coordinates conversion portion 25 converts position and direction data that is stored in the distal end position storage portion 24 to three-dimensional data coordinate values based on the conversion formula calculated by the position alignment portion 23. The coordinates conversion portion 25 then stores the post-conversion position and direction data for the distal end of the insertion portion 11 after conversion in the distal end position storage portion 24 together with the pre-conversion position and direction data and the time stamp TS. For example, in the example shown in FIG. 3, the coordinates conversion portion 25 converts coordinate values A1, B1, and C1 of position data with respect to real space for the time stamp TS1 to coordinate values D1, E1, and F1, respectively, for three-dimensional data based on the conversion formula calculated by the position alignment portion 23.

Thus, a position alignment portion is constructed that makes position information of the distal end of the insertion portion 11 that is acquired by the position detection apparatus 4 correspond to position information of three-dimensional image coordinates of a predetermined luminal organ by means of the position alignment portion 23 and the coordinates conversion portion 25.

Note that the method of position alignment is not limited to a position alignment method that uses the above described conversion formula, and a method may also be adopted that extracts the shape of the renal pelvis and renal calices from an X-ray image that is taken in from the X-ray C-arm apparatus 5, calculates position coordinates of the renal pelvis and renal calices that were extracted from X-ray photographing position data from the position detection apparatus, and performs position alignment with respect to position coordinates of the renal pelvis and renal calices in three-dimensional data. Furthermore, position alignment may also be performed by detecting positions of feature points on the body surface of a patient and specifying feature points in three-dimensional data as disclosed in Japanese Patent Application Laid-Open Publication No. 2005-312770, or by matching an endoscopic image and a virtual endoscopic image as disclosed in Japanese Patent Application Laid-Open Publication No. 2009-279251.

The determination portion 26 compares coordinate values on the three-dimensional data 31 converted in the above manner and renal calices coordinates data extracted by the image processing portion 22, and determines whether or not the distal end of the insertion portion 11 reached the renal calices 42 to 49. The determination portion 26 outputs the result of the determination to the image processing portion 22. In addition, a configuration may also be adopted in which the determination portion 26 determines whether or not the image pickup portion passed through a duct inside a predetermined luminal organ, and not only through the renal calices 42 to 49.

The image processing portion 22 generates an insertion trail 50 of the distal end of the insertion portion 11 by connecting the coordinate values in the three-dimensional data 31 stored in the distal end position storage portion 24 with a solid line, and superimposes the insertion trail 50 on the three-dimensional data 31 and 32.

The image processing portion 22 also generates distal end position information 51 regarding the current position of the distal end of the insertion portion 11 (distal end of the insertion trail 50), and superimposes the distal end position information 51 on the three-dimensional data 31 and 32.

In addition, the image processing portion 22 generates determination information 52 for determining whether or not the renal calices 42 to 49 were observed, based on the determination result from the determination portion 26, and superimposes the determination information 52 on the three-dimensional data 31 and 32. As shown in FIG. 4, for example, the determination information 52 uses a black circle to show the renal calices 42 to 46 that the distal end of the insertion portion 11 reached, and uses a white circle to show the renal calices 47 to 49 that the distal end of the insertion portion 11 has not reached.

The image processing portion 22 converts the three-dimensional data 31 and 32 on which the insertion trail 50, the distal end position information 51, and the determination information 52 are superimposed into two-dimensional data to enable display thereof on the display apparatus 8, and outputs the resulting data to the display apparatus 8. The image processing portion 22 also superimposes the insertion trail 50, the distal end position information 51, and the determination information 52 on the virtual endoscopic image 33 and the endoscopic image 34, and outputs the resulting data to the display apparatus 8. Note that, in the example shown in FIG. 4, only the insertion trail 50 is superimposed on the virtual endoscopic image 33 and the endoscopic image 34 and displayed.

Figure 5:
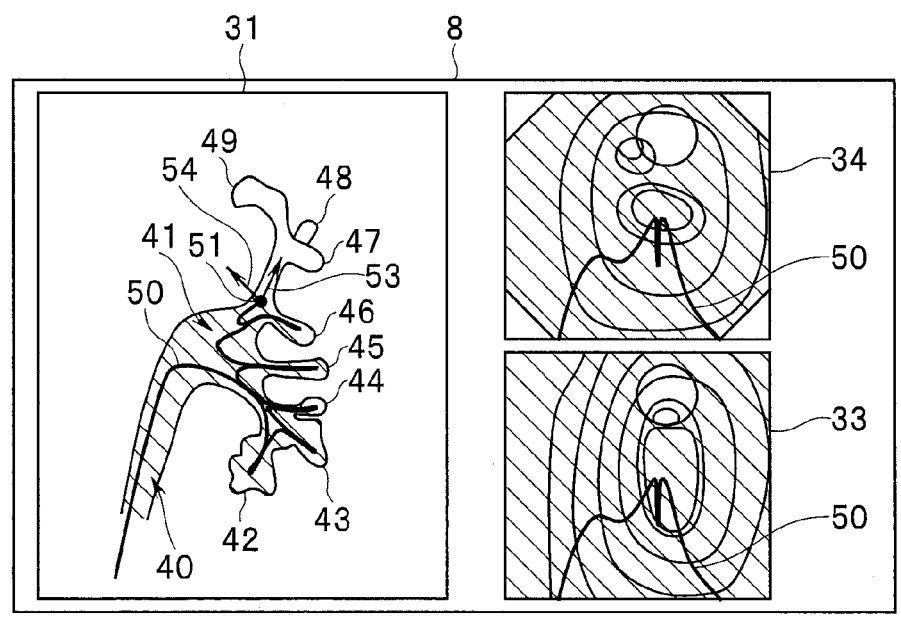
FIG. 5 is an explanatory view for describing another example of an image that is displayed on the display apparatus 8.

Note that the determination information 52 is not limited to the black circles and white circles shown in FIG. 4. For example, as shown in FIG. 5, the image processing portion 22 may also be configured to change a color of a place that the distal end of the insertion portion 11 reached (in FIG. 5, a place at which the color was changed is indicated by diagonal lines). In the example in FIG. 5, the color of the ureter 40, the renal pelvis 41, and the renal calices 42 to 46 which the distal end of the insertion portion 11 reached is changed to a different color than the color of the renal calices 47 to 49 that the distal end of the insertion portion 11 has not reached. In this manner, the image processing portion 22 changes the display form of the three-dimensional data 31 and 32, the virtual endoscopic image 33, and the endoscopic image 34 based on the determination information 52.

Further, based on position and direction data stored in the distal end position storage portion 24, the image processing portion 22 generates an arrow 53 that shows the orientation of the distal end of the insertion portion 11 (in the case of a front-view type endoscope, the line-of-sight direction of the endoscopic image) and an arrow 54 that indicates the upward direction of the endoscopic image, and displays the arrows 53 and 54 in a superimposed manner on the three-dimensional data 31. As a result, it is easy for a user to recognize the insertion/withdrawal direction of the insertion portion 11 and the direction from which the endoscopic image is being viewed.

Figure 6:
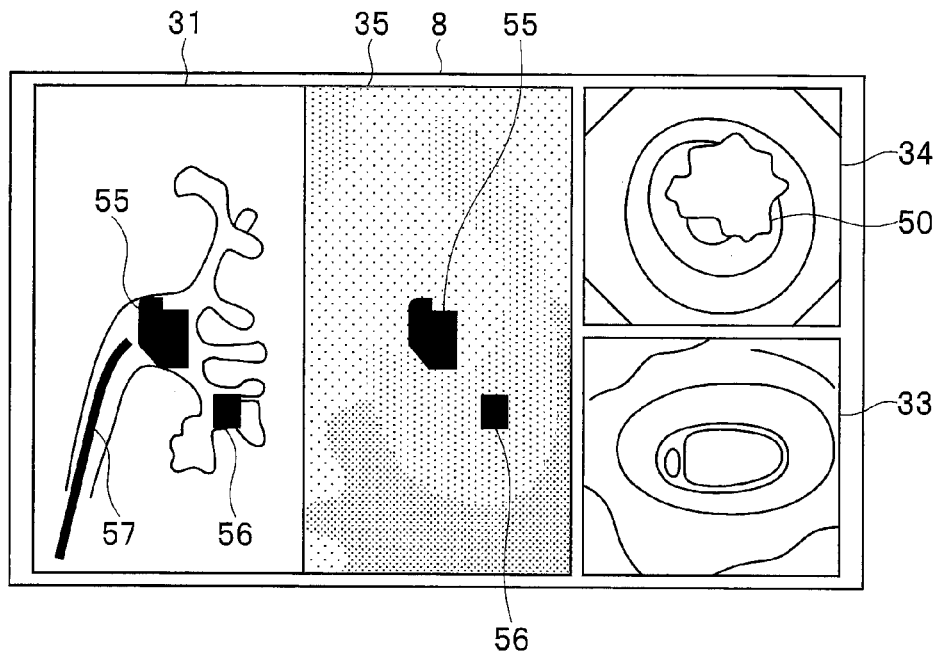
FIG. 6 is an explanatory view for describing another example of an image that is displayed on the display apparatus 8.

Next, processing that displays a predetermined structure is described using FIG. 6.

The X-ray image acquisition portion 27 acquires X-ray image data during an operation from the X-ray C-arm apparatus 5, and outputs the X-ray image data to the image processing portion 22 and the calculi coordinates calculation portion 28. The image processing portion 22 performs predetermined image processing on the X-ray image data from the X-ray image acquisition portion 27 to generate an X-ray image 35, and performs control to display the generated X-ray image 35 on the display apparatus 8. For example, in the example shown in FIG. 6, the X-ray image 35 is displayed on the display apparatus 8 instead of the three-dimensional data 32 shown in FIG. 4.

X-ray image data from the X-ray image acquisition portion 27 and X-ray photographing position data from the position detection apparatus 4 are inputted to the calculi coordinates calculation portion 28. The calculi coordinates calculation portion 28 performs analysis of the X-ray image data and calculates positions of predetermined structures on the X-ray image 35. In the example shown in FIG. 6, the predetermined structures are calculi 55 and 56. The calculi coordinates calculation portion 28 then calculates existence ranges of the calculi 55 and 56 with respect to real space coordinates based on the positions of the calculi 55 and 56 on the X-ray image 35 and the X-ray photographing position data. If there is X-ray image data that was photographed from a plurality of directions, for example, two directions, the calculi coordinates calculation portion 28 narrows down the existence ranges of the calculi 55 and 56 based on the respective existence ranges of the calculi 55 and 56, and calculates three-dimensional positions and shapes of the calculi 55 and 56. The calculated existence ranges of the calculi 55 and 56 are outputted to the calculi coordinates conversion portion 29. Thus, the calculi coordinates calculation portion 28 constitutes an extraction portion that extracts a predetermined structure from X-ray image data.

The calculi coordinates conversion portion 29 converts the existence ranges of the calculi 55 and 56 with respect to the real space coordinates to existence ranges of the calculi 55 and 56 with respect to three-dimensional data coordinates based on the conversion formula calculated by the position alignment portion 23. The calculi coordinates conversion portion 29 outputs the coordinates of the existence ranges of the calculi 55 and 56 after conversion to the determination portion 26 as calculi coordinates data. Note that a configuration may also be adopted in which the calculi coordinates conversion portion 29 is not provided, and the coordinates conversion portion 25 converts the existence ranges of the calculi 55 and 56 with respect to real space coordinates to existence ranges of the calculi 55 and 56 with respect to three-dimensional data coordinates.

The determination portion 26 compares position and direction data for which a reset flag is not set among the post-conversion position and direction data stored in the distal end position storage portion 24 and calculi coordinates data from the calculi coordinates conversion portion 29 to determine whether or not the distal end of the insertion portion 11 reached the respective calculi 55 and 56. The determination portion 26 outputs the result of the determination to the image processing portion 22.

Based on the converted position and direction data, the image processing portion 22 superimposes determination information indicating whether or not the distal end of the insertion portion 11 reached the calculi 55 and 56. As the determination information, for example, the image processing portion 22 colors the calculus 55 for which the distal end of the insertion portion 11 was determined to have reached in a different color than the color of the calculus 56 which the distal end was determined to have not reached. Note that the image processing portion 22 may also be configured to erase the calculus 55 which was determined as having being reached by the distal end of the insertion portion 11 from the three-dimensional data 31 based on the determination result.

The image processing portion 22 also superimposes an insertion shape 57 of the insertion portion 11 on the three-dimensional data 31. To calculate the insertion shape 57, positions for real space coordinates are calculated based on electrical signals from the plurality of reception coils that are provided at predetermined intervals in the insertion portion 11, and the position data is converted to coordinates data for three-dimensional data using the conversion formula. The image processing portion 22 then generates the insertion shape 57 by connecting the coordinates data with a solid line, and superimposes the insertion shape 57 on the three-dimensional data 31.

In accordance with a user instruction, the image processing portion 22 performs image processing of the three-dimensional data 31 on which the calculi 55 and 56 and the insertion shape 57 are displayed in a superimposed manner to thereby create a two-dimensional image to be displayed on the display apparatus 8, and outputs the created two-dimensional image to the display apparatus 8.

Figure 7:
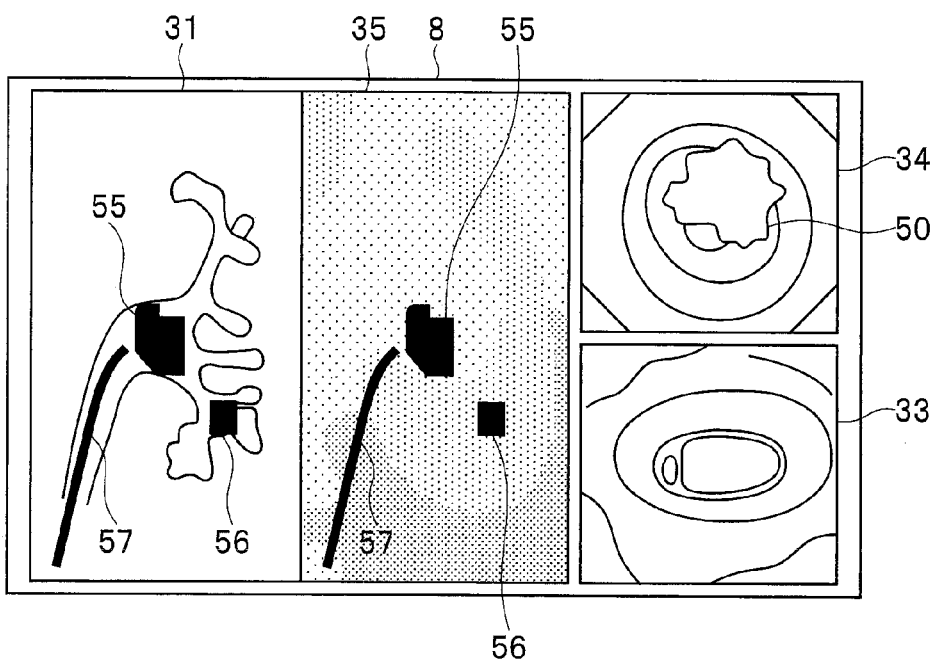
FIG. 7 is an explanatory view for describing another example of an image that is displayed on the display apparatus 8.

Note that the image processing portion 22 may be configured to superimpose not only the calculi 55 and 56 and the insertion shape 57 on the three-dimensional data 31, but to also superimpose the above described insertion trail 50 of the distal end of the insertion portion 11, the distal end position information 51, and the determination information 52 on the three-dimensional data 31. As one example of a method of superimposing the determination information 52, a method may be adopted that displays the calculus 55 which the distal end was determined to have reached or passed through in a semi-transparent manner on the three-dimensional data 31. Further, as shown in FIG. 7, the image processing portion 22 may be configured so as to superimpose the insertion shape 57 on the X-ray image 35, and display the resulting image on the display apparatus 8.

Figure 8:
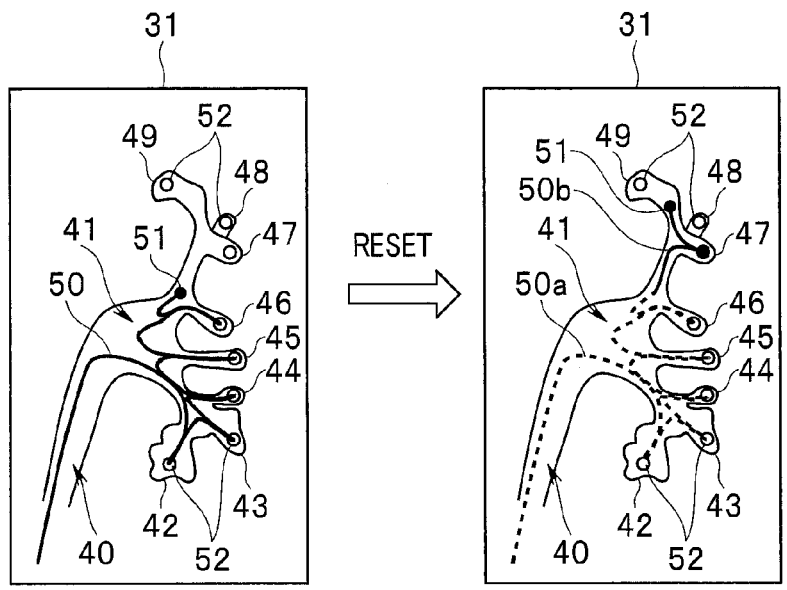
FIG. 8 is an explanatory view for describing a further example of an image that is displayed on the display apparatus 8.

Next, reset processing will be described using FIG. 3 and FIG. 8.

When the user performs a reset operation using an unshown switch that is provided on the operation portion 12, a reset signal is inputted to the image processing apparatus 7. When the reset signal is inputted, a reset flag is set for all of the data stored in the distal end position storage portion 24.

For example, when a reset signal is inputted at the time point of a time stamp TS4, a reset flag is set for time stamps TS1 to TS4. In the example shown in FIG. 3, data for which a reset flag is set is indicated by "○", and data for which a reset flag is not set is indicated by "–". The data for a time stamp ST5 and thereafter for which a reset flag is not set is position data of the distal end of the insertion portion 11 that was newly stored in the distal end position storage portion 24 after the reset signal was inputted.

The image processing portion 22 resets the display of data for which a reset flag is set among the data stored in the distal end position storage portion 24. For example, as shown in FIG. 8, the image processing portion 22 changes the display of the insertion trail 50 that was displayed prior to the reset operation from a solid line to a dashed line (insertion trail 50a), and changes the determination information 52 from black circles to white circles. Further, the image processing portion 22 displays the trail of the distal end of the insertion portion 11 after the reset operation (from the time stamp ST5 onward) using a solid line (insertion trail 50b), and changes determination information 52 of the renal calix 47 that the distal end of the insertion portion 11 reached after the reset operation from white circles to black circles. Note that the image processing portion 22 may also be configured to change the colors of the insertion trail 50a and insertion trail 50b with respect to before and after the reset operation, or to not display the insertion trail 50a that existed prior to the reset operation.

In this kind of treatment of the renal pelvis 41 and the renal calices 42 to 49, if the calculi 55 and 56 are a large size, the calculi 55 and 56 are removed after crushing the calculi 55 and 56 into pieces using an unshown treatment instrument. In this case, since there is a possibility that the crushed pieces of calculi will enter one or more of the renal calices that were already examined (for example, renal calices 42 to 46 in FIG. 4), it is necessary to also re-examine the renal calices 42 to 46 that were previously examined. Therefore, a configuration is adopted that resets the insertion trail 50 and determination information 52 by performing reset processing so that the renal calices 42 to 46 can be examined again to ensure none of the renal calices 42 to 46 are overlooked in the examination.

To improve the visibility, the image processing portion 22 may be configured so as not to display the insertion trail 50 at places that the insertion portion 11 has passed through in the ureter 40, the renal pelvis 41, and the renal calices 42 to 49.

Figure 9:
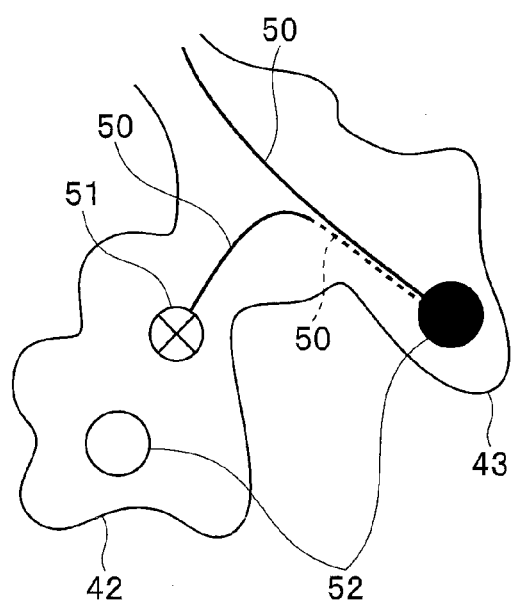
FIG. 9 is an explanatory view for describing an example of processing of an image processing portion 22 that improves visibility.

FIG. 9 is an explanatory view for describing an example of processing of the image processing portion 22 that improves the visibility.

As shown in FIG. 9, in a case where the insertion trail 50 was displayed when the insertion portion 11 was inserted into the renal calix 43, the image processing portion 22 does not display the insertion trail 50 when withdrawing the insertion portion 11 from the renal calix 43. Note that in the example shown in FIG. 9, the insertion trail 50 that is not displayed is indicated by a thin dashed line. More specifically, the determination portion 26 determines whether or not the current position of the distal end of the insertion portion 11 is a place that the distal end has passed through once, and if the determination portion 26 determines that the distal end already passed through the current position once, the image processing portion 22 performs processing so that the insertion trail 50 is not displayed.

The determination portion 26 uses centerline data of the lumen in the three-dimensional data 31 to determine whether or not the current position of the distal end of the insertion portion 11 is a place that the distal end has already passed through once. Specifically, the determination portion 26 makes the determination as follows. First, with respect to each of the position coordinates of the distal end of the insertion portion 11 that are stored in the distal end position storage portion 24, the determination portion 26 takes a point on the nearest centerline data as a trail point. Next, among the centerline data, the determination portion 26 displays an insertion trail on centerline data of a range in which the trail points exist. Consequently, whichever positions are passed through, by displaying an insertion trail on the centerline regardless of which positions the scope has actually passed inside the lumen, if the distal end of the insertion portion 11 passes again through a lumen that the distal end already passed through once, the insertion trail 50 is not displayed in a twofold manner and therefore the visibility can be improved.

Another method will now be described that ensures that the insertion trail 50 is not displayed when it is determined that the position of the distal end of the insertion portion 11 is a place that the distal end has already passed through. This is a method that does not use centerline information. First, the determination portion 26 calculates distances between past positions of the distal end of the insertion portion 11 that are stored in the distal end position storage portion 24 and the current position of the distal end of the insertion portion 11, and determines whether or not the value of the shortest distance among the calculated distances is greater than a predetermined threshold value. If it is determined that the value of the shortest distance that was calculated is greater than the predetermined threshold value, the determination portion 26 determines that the current position of the distal end is not a position that the distal end has already passed through, and displays the insertion trail 50 in the image processing portion 22. In contrast, if it is determined that the value of the shortest distance that was calculated is less than or equal to the predetermined threshold value, the determination portion 26 determines that the current position of the distal end is a position that the distal end has already passed through, and does not display the insertion trail 50 in the image processing portion 22. As a result of this processing of the image processing portion 22, the visibility can be improved because the same place is not displayed as part of a trail many times.

Figure 10:
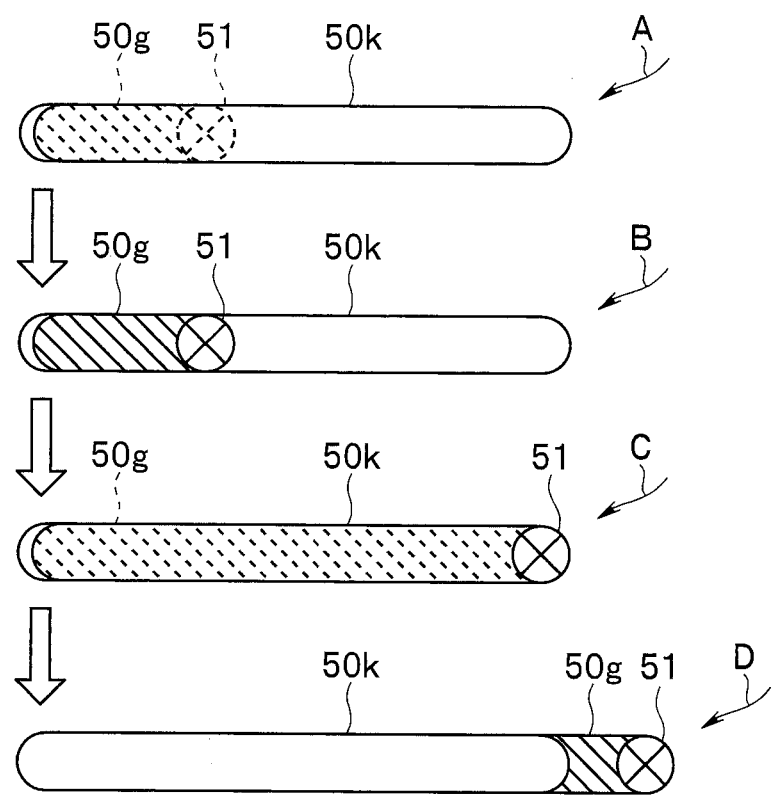
FIG. 10 is an explanatory view for describing another example of processing of the image processing portion 22 that improves visibility.

The image processing portion 22 may also improve the visibility of the insertion portion 11 by performing the processing shown in FIG. 10. FIG. 10 is an explanatory view for describing another example of processing of the image processing portion 22 that improves visibility.

To prevent confusion with respect to the illustration in FIG. 10 and the following description, the "insertion trail 50" is described by separating the insertion trail 50 into a "past insertion trail 50k" and a "current insertion trail 50g". As shown by an arrow A in FIG. 10, in the three-dimensional data 31, in the case of inserting the insertion portion 11 along a different route that is parallel to the insertion trail 50 and is on the inner side in the direction of FIG. 10, the current insertion trail 50g and the distal end position information 51 (or insertion shape 57) are displayed on the rear side of the past insertion trail 50k. In this case, the user is not able to confirm the current position of the insertion portion 11 and thus the visibility is poor. Note that, in the example indicated by the arrow A in FIG. 10, the current insertion trail 50g and the distal end position information 51 that are hidden by the past insertion trail 50k are indicated by thin dashed lines.

Therefore, as shown by an arrow B in FIG. 10, the image processing portion 22 is configured to improve the visibility of the current route by displaying the current insertion trail 50g and the distal end position information 51 (indicated by solid lines) on the front side relative to the past insertion trail 50k.

Further, as shown by an arrow C in FIG. 10, when the past insertion trail 50k and the current insertion trail 50g become the same length, the image processing portion 22 displays the distal end position information 51 on the front side relative to the past insertion trail 50k, and displays the current insertion trail 50g (indicated by a dashed line) in a transparent state. In addition, as shown by an arrow D in FIG. 10, if the position of the distal end of the insertion portion 11 is no longer hidden by the past insertion trail 50k, the image processing portion 22 displays the current insertion trail 50g and the distal end position information 51 on the rear side of the past insertion trail 50k.

The image processing portion 22 performs the above display control to generate the past insertion trail 50k and the current insertion trail 50g so as to be distinguishable from each other. By the afore described processing of the image processing portion 22, a situation can be prevented in which the route that is currently being depicted (insertion trail 50g) is not displayed due to being hidden by the past insertion trail 50k that was already generated, and thus the visibility can be improved. The display control is not limited to the above described control, and display control may also be performed so as to semitransparently display a portion of the past insertion trail 50k that is in front of the current insertion trail 50g.

An unshown storage portion is further provided in the image processing apparatus 7. The insertion trail 50 of the distal end of the insertion portion 11, that is, position data of the distal end of the insertion portion 11 stored in the distal end position storage portion 24 is stored in the unshown storage portion. When performing a re-examination, the image processing portion 22 reads out position data of the previous examination that is stored in the storage portion and displays the insertion trail 50 of the previous examination.

In this case, the image processing portion 22 changes the display form of the insertion trail 50 of the previous examination to a display form that is different than that of the insertion trail 50 of the current examination. For example, the image processing portion 22 displays the insertion trail 50 of the previous examination as a dotted line, and displays the insertion trail 50 of the previous examination in a different color than the color of the insertion trail 50 of the current examination. In addition, the image processing portion 22 may perform the processing of FIG. 10 that is described above to prevent the insertion trail 50 of the current examination from being hidden by the insertion trail 50 of the previous examination and no longer displayed.

Furthermore, the image processing portion 22 may be configured to perform the following processing as a method that improves the visibility of the insertion portion 11. The image processing portion 22 may display the insertion trail 50 of the route on a frontward side on the three-dimensional data 31 in a thin manner, and may display the insertion trail 50 of the route on the inner side in a thick manner. For example, in the three-dimensional data 31 shown in FIG. 4, since the renal calix 48 is present on a route that is further on the inner side than the renal calix 47, the image processing portion 22 displays the insertion trail 50 to the renal calix 48 in a thick manner and displays the insertion trail 50 to the renal calix 47 in a thin manner.

The image processing portion 22 may perform similar processing with respect to the distal end position information 51. For example, in a case where the current position of the insertion portion 11 is on a route on the frontward side, the image processing portion 22 displays a line of the distal end position information 51 in a thin manner or displays the diameter thereof in a small form, and in a case where the current position of the insertion portion 11 is on a route on the inner side, the image processing portion 22 displays a line of the distal end position information 51 in a thick manner or displays the diameter thereof in a large form. Consequently, the occurrence of situations in which a current position or an insertion trail that is on the inner side cannot be seen due to an obstruction such as an insertion trail that is on the frontward side can be reduced, and thus the visibility of the user improves.

Next, operations of the endoscope system 1 configured in this manner are described.

Figure 11:
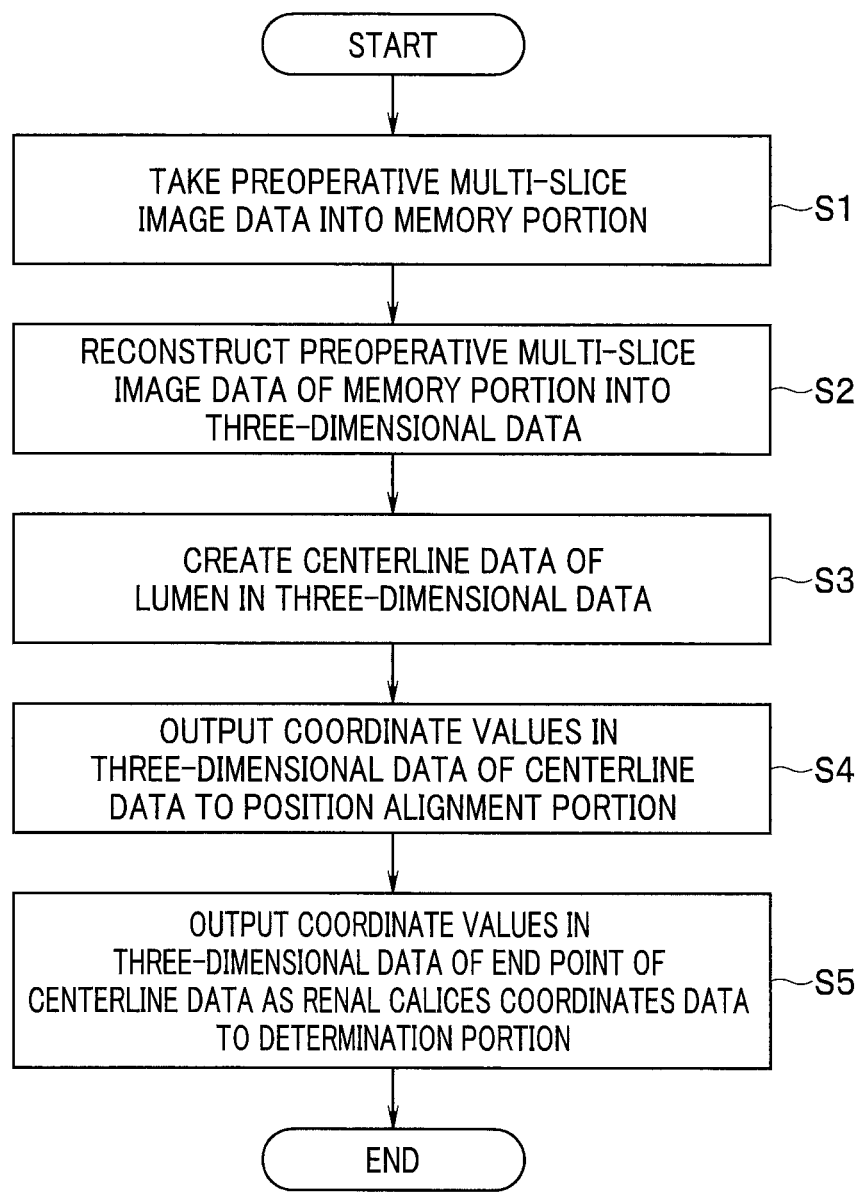
FIG. 11 is a flowchart that illustrates an example of the flow of preoperative image processing.

Preoperative image processing will be described first. FIG. 11 is a flowchart that illustrates an example of the flow of the preoperative image processing.

First, the image processing apparatus 7 takes the preoperative multi-slice image data 16a to 16n into the memory portion 21 (step S1). Next, the image processing portion 22 reconstructs the preoperative multi-slice image data 16a to 16n of the memory portion 21 into the three-dimensional data 31 (step S2). The image processing portion 22 then creates centerline data of the lumen in the three-dimensional data 31 (step S3), and outputs coordinate values of the centerline data in the three-dimensional data 31 to the position alignment portion 23 (step S4). Finally, the image processing portion 22 outputs the coordinate values with respect to the three-dimensional data 31 of the end point of the centerline data as renal calices coordinates data to the determination portion 26 (step S5), and ends the processing.

Figure 12:
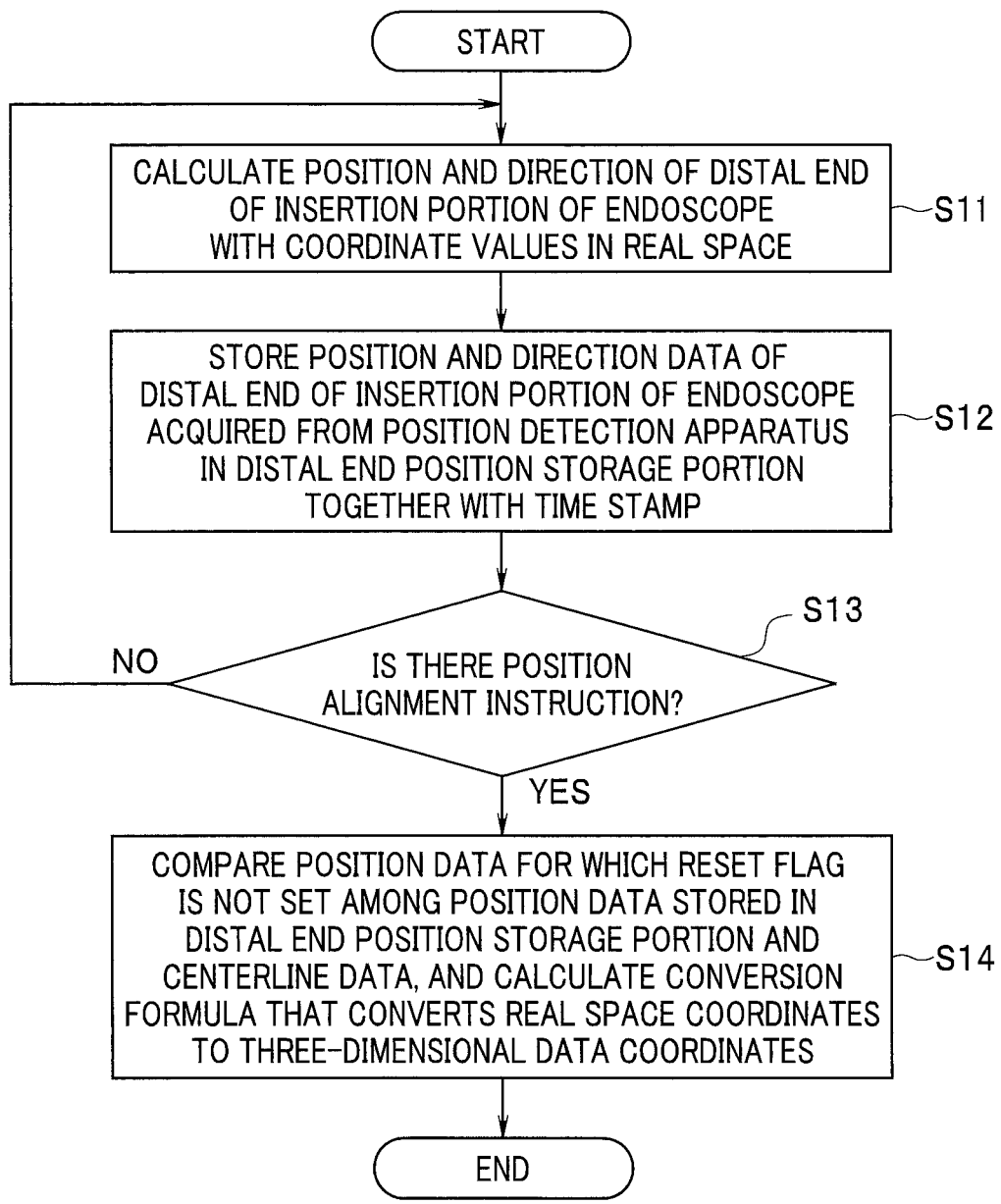
FIG. 12 is a flowchart that illustrates an example of the flow of position alignment processing.

Next, position alignment processing will be described. FIG. 12 is a flowchart that shows an example of the flow of the position alignment processing.

First, the position detection apparatus 4 calculates the position and direction of the distal end of the insertion portion 11 of the endoscope 2 with coordinate values in real space (step S11). The image processing apparatus 7 stores position and direction data of the distal end of the insertion portion 11 of the endoscope 2 that is acquired from the position detection apparatus 4 in the distal end position storage portion 24 together with the time stamp ST (step S12).

Next, it is determined whether or not there is an instruction to perform position alignment (step S13). If it is determined that an instruction to perform position alignment was not received, the determined result is "No" and the operation returns to step S11 to repeat the same processing. In contrast, if it is determined that an instruction to perform position alignment was received, the determined result is "Yes", and therefore the position alignment portion 23 compares position data for which a reset flag is not set among position data stored in the distal end position storage portion 24 and the centerline data, and calculates a conversion formula that converts the real space coordinates to three-dimensional data coordinates (step S14). Thereafter, the processing is ended.

Figure 13:
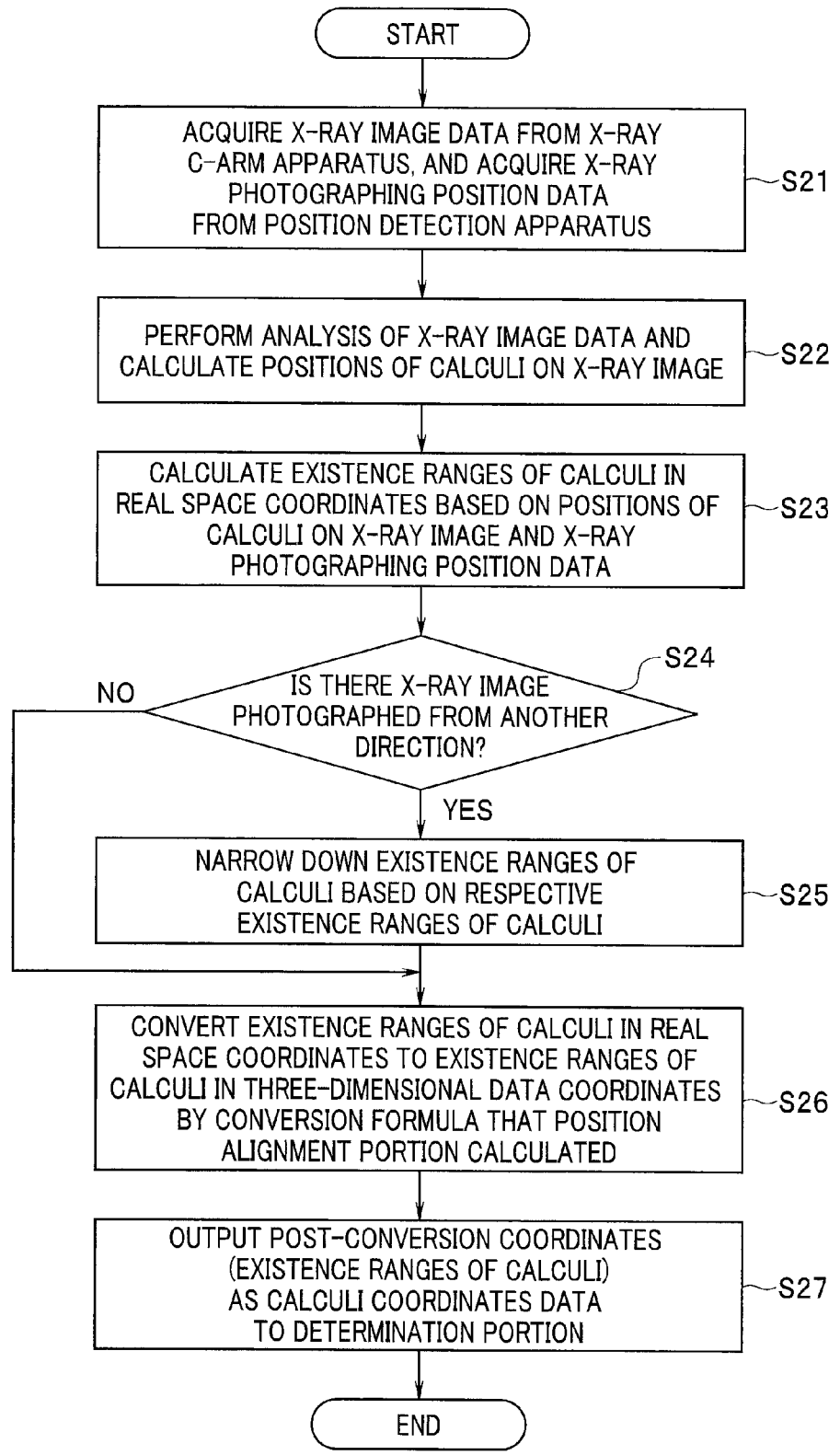
FIG. 13 is a flowchart that illustrates an example of the flow of processing to analyze a predetermined structure.

Next, processing to analyze predetermined structures (the calculi 55 and 56) is described. FIG. 13 is a flowchart that illustrates an example of the flow of the processing to analyze predetermined structures.

First, the image processing apparatus 7 acquires X-ray image data from the X-ray C-arm apparatus 5 and acquires X-ray photographing position data from the position detection apparatus 4 (step S21). The calculi coordinates calculation portion 28 performs an analysis of the X-ray image data to calculate the positions of the calculi 55 and 56 on the X-ray image 35 (step S22). Next, the calculi coordinates calculation portion 28 calculates existence ranges of the calculi 55 and 56 with respect to real space coordinates based on positions of the calculi 55 and 56 on the X-ray image 35 and the X-ray photographing position data (step S23).

Next, it is determined whether or not there is an X-ray image that was photographed from another direction (step S24). If there is not an X-ray image that was photographed from another direction, the determined result is "No", and the operation advances to step S26. In contrast, if there is an X-ray image that was photographed from another direction, the determined result is "Yes", and the existence ranges of the calculi 55 and 56 are narrowed down based on the respective existence ranges of the calculi 55 and 56 (step S25). The calculi coordinates conversion portion 29 converts the existence ranges of the calculi 55 and 56 with respect to the real space coordinates to existence ranges of the calculi with respect to three-dimensional data coordinates by the conversion formula that the position alignment portion 23 calculated (step S26). Finally, the calculi coordinates conversion portion 29 outputs the post-conversion coordinates (existence ranges of the calculi) as calculi coordinates data to the determination portion 26 (step S27), and ends the processing.

Figure 14:
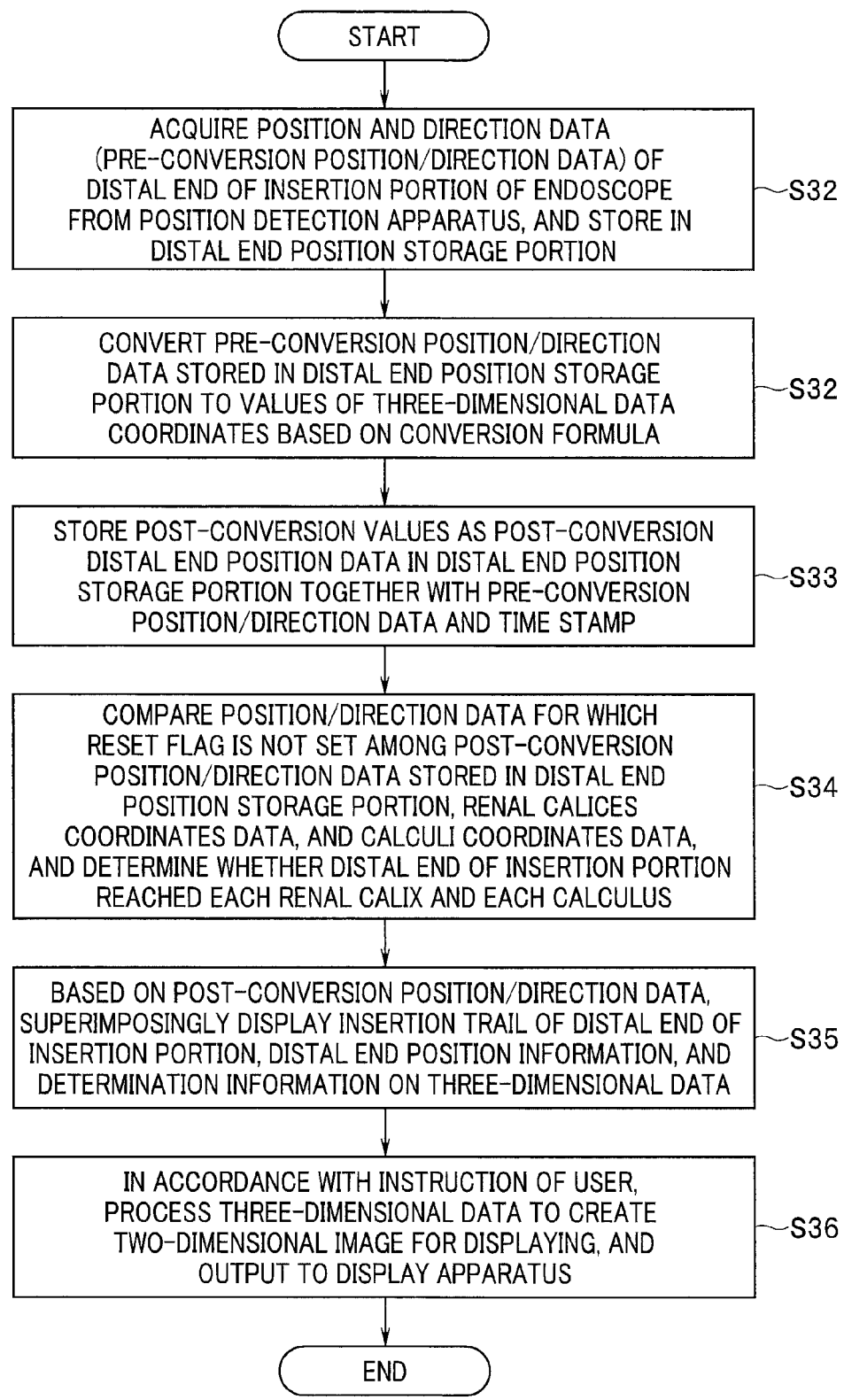
FIG. 14 is a flowchart that illustrates an example of the flow of navigation processing.

Next, navigation processing is described. FIG. 14 is a flowchart that illustrates an example of the flow of the navigation processing.

First, the image processing apparatus 7 acquires position and direction data (hereunder, also referred to as "pre-conversion position/direction data") of the distal end of the insertion portion 11 of the endoscope 2 from the position detection apparatus 4, and stores the acquired data in the distal end position storage portion 24 (step S31). The coordinates conversion portion 25 converts the pre-conversion position/direction data stored in the distal end position storage portion 24 to values for three-dimensional data coordinates based on the conversion formula (step S32). The coordinates conversion portion 25 stores the post-conversion values as post-conversion position/direction data in the distal end position storage portion 24 together with the pre-conversion position/direction data and the time stamp TS (step S33).

The determination portion 26 compares position and direction data for which a reset flag is not set among the post-conversion position/direction data stored in the distal end position storage portion 24, renal calices coordinates data, and calculi coordinates data to determine whether the distal end of the insertion portion 11 reached each of the renal calices 42 to 49 and each of the calculi 55 and 56 (step S34). Based on the post-conversion position/direction data, the image processing portion 22 superimposingly displays the insertion trail 50 of the distal end of the insertion portion 11, the distal end position information 51 (current position of the distal end of the insertion portion 11), and the determination information 52 that was determined in step S34 on the three-dimensional data 31 (step S35). In accordance with an instruction of the user, the image processing portion 22 processes the three-dimensional data to create a two-dimensional image for displaying, outputs the created two-dimensional image to the display apparatus 8 (step S36), and then ends the processing.

Figure 15:
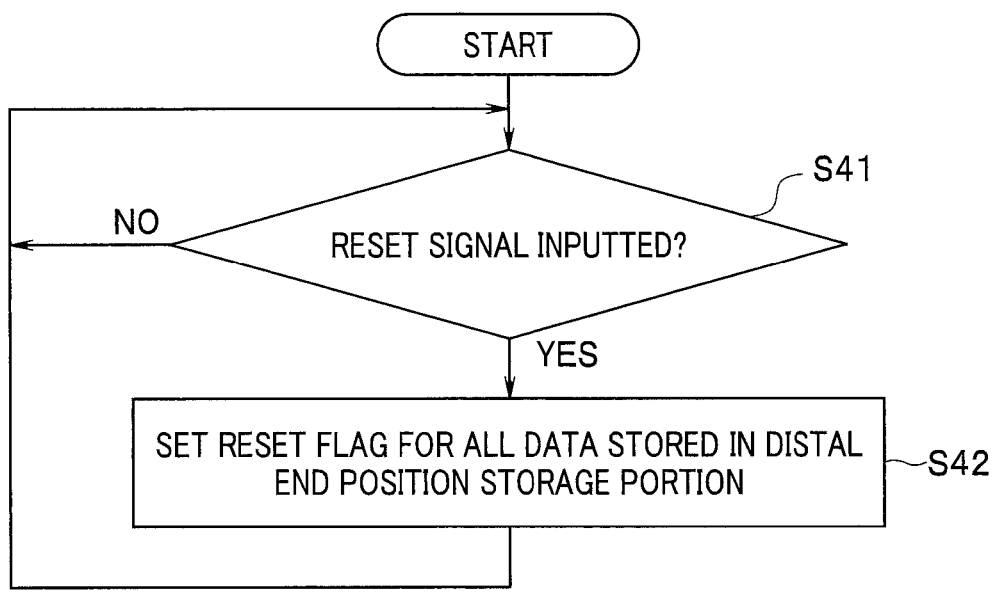
FIG. 15 is a flowchart that illustrates an example of the flow of reset processing.

Next, reset processing when a reset signal is inputted is described. FIG. 15 is a flowchart that illustrates an example of the flow of the reset processing.

First, it is determined whether or not a reset signal was inputted (step S41). If it is determined that a reset signal has not been inputted, the determined result is "No" and the operation returns to step S41 to repeat the same processing. In contrast, if it is determined that a reset signal has been inputted, the determined result is "Yes", and thus a reset flag is set for all data that is stored in the distal end position storage portion 24, and thereafter the operation returns to step S41 to repeat the same processing (step S42).

As described above, the endoscope system 1 is configured so as to construct the three-dimensional data 31 of a predetermined luminal organ that includes the ureter 40, the renal pelvis 41, and the renal calices 42 to 49, and so as to also superimpose the insertion trail 50 of the distal end of the insertion portion 11, the distal end position information 51 of the distal end of the insertion portion 11, and the determination information 52 that indicates whether or not the distal end of the insertion portion 11 has reached relevant positions on the three-dimensional data 31, and display the resulting data on the display apparatus 8. As a result, a user can easily recognize whether or not the entire inside of the predetermined luminal organ was examined using the endoscope 2.

Hence, according to the endoscope system of the present embodiment, a user can easily distinguish whether or not a place was observed with an endoscope.

Second Embodiment

Next, a second embodiment will be described.

Figure 16:
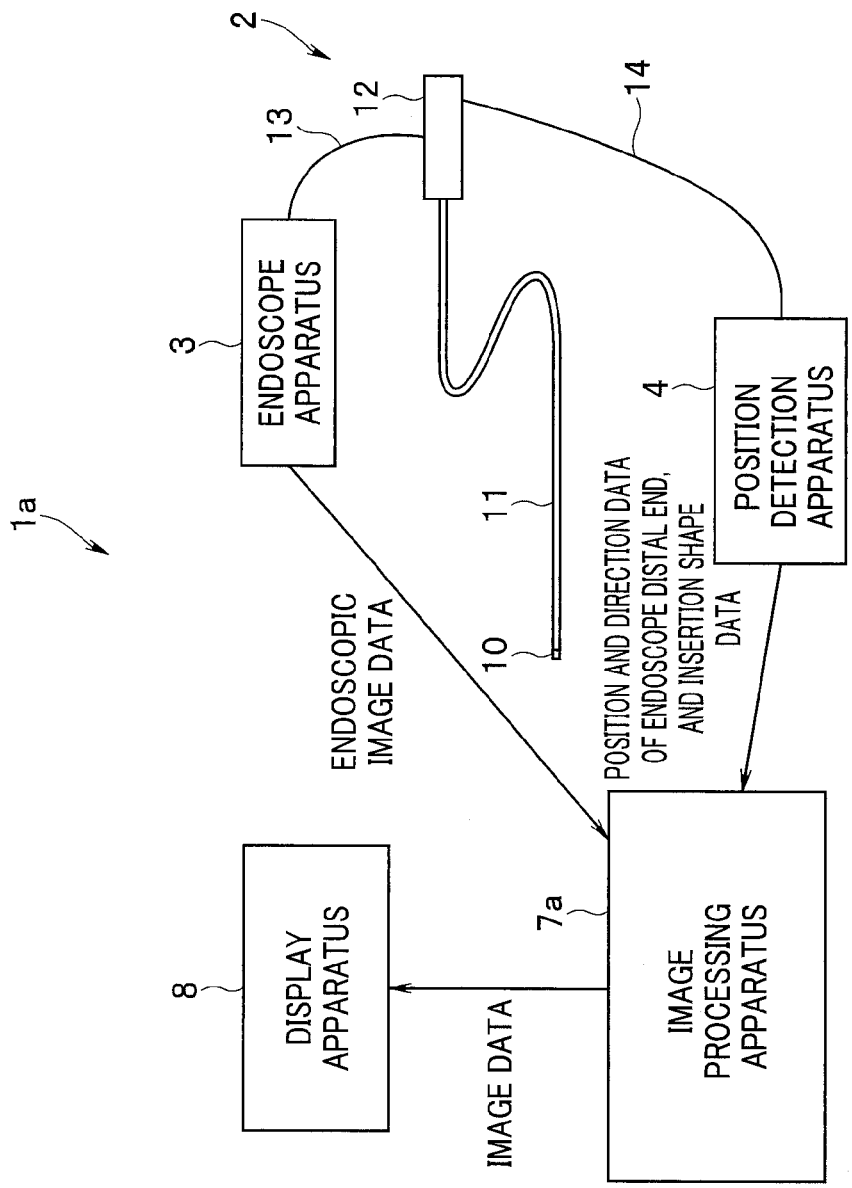
FIG. 16 is a configuration diagram that illustrates the configuration of an endoscope system according to a second embodiment.

According to the second embodiment, an endoscope system is described that generates an insertion trail in a case where there is no three-dimensional data and an insertion route is not known. FIG. 16 is a configuration diagram that shows the configuration of the endoscope system according to the second embodiment.

As shown in FIG. 16, relative to the endoscope system 1 shown in FIG. 1, the X-ray C-arm apparatus 5, the server 6, the cable 15, and the preoperative multi-slice image data 16a to 16n are not included in an endoscope system 1a. Further, the endoscope system 1a uses an image processing apparatus 7a instead of the image processing apparatus 7 shown in FIG. 1.

Figure 17:
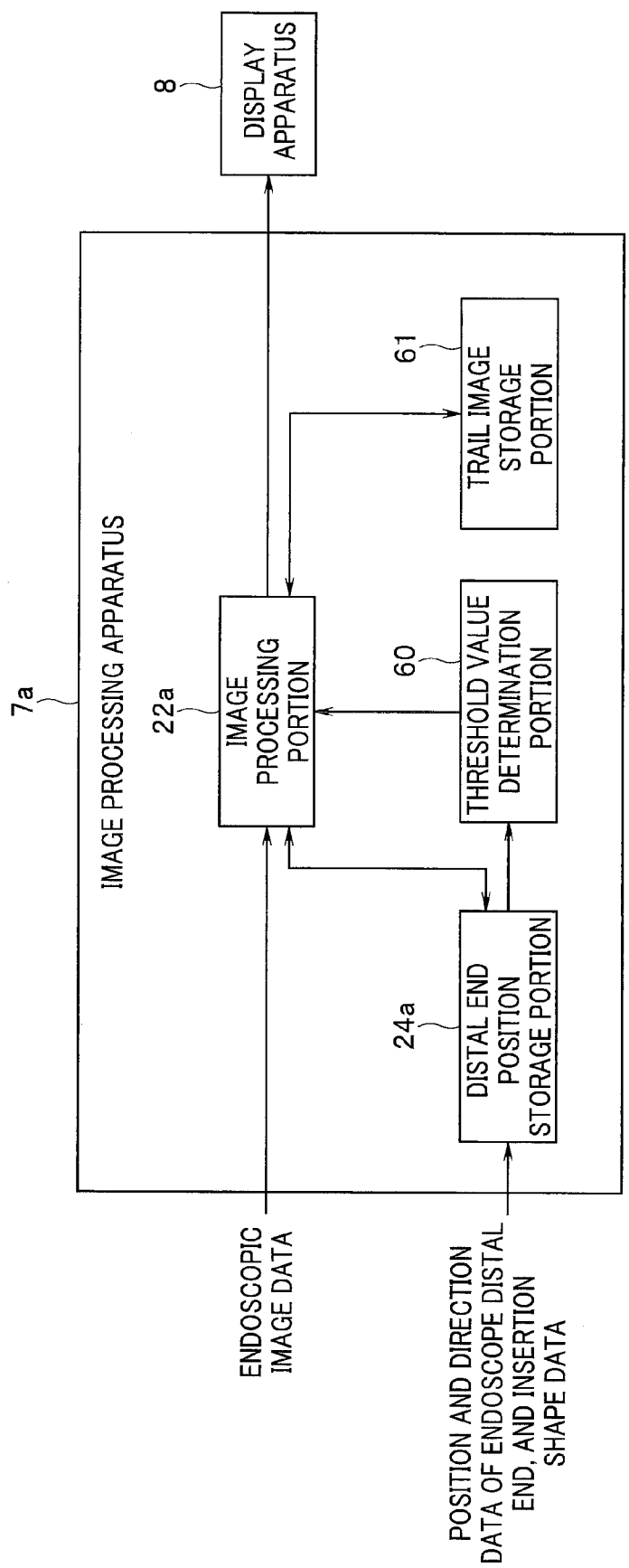

FIG. 17 is a configuration diagram for describing the detailed configuration of the image processing apparatus 7a.

The image processing apparatus 7a includes an image processing portion 22a, a distal end position storage portion 24a, a threshold value determination portion 60, and a trail image storage portion 61.

Position data with respect to real space of the distal end of the insertion portion 11 that was outputted from the position detection apparatus 4 is stored in the distal end position storage portion 24a together with the time stamp TS. In the case of displaying the direction of the distal end of the insertion portion 11 or the insertion shape of the insertion portion 11 on the display apparatus 8, direction data and insertion shape data detected by the position detection apparatus 4 are also stored in the distal end position storage portion 24a.

The image processing portion 22a uses the position data stored in the distal end position storage portion 24a as it is to map coordinate values with respect to three-dimensional data and generate an insertion trail. At this time, the image processing portion 22a performs the processing so as not to display the insertion trail at places that were already passed through once, based on the determination result of the threshold value determination portion 60.

The threshold value determination portion 60 calculates a distance between past positions of the distal end of the insertion portion 11 that are stored in the distal end position storage portion 24a and the current position of the distal end of the insertion portion 11, and determines whether or not the value of the shortest distance among the calculated distances is greater than a predetermined threshold value. That is, the threshold value determination portion 60 determines whether or not the current position of the distal end of the insertion portion 11 is separated by a predetermined threshold value from positions that the distal end of the insertion portion 11 passed through in the past. The threshold value determination portion 60 outputs the determination result to the image processing portion 22a.

If the threshold value determination portion 60 determines that the value of the shortest distance is greater than the predetermined threshold value, the image processing portion 22a determines that the current position of the distal end of the insertion portion 11 is not a place that was passed once, and displays the insertion trail. In contrast, if the threshold value determination portion 60 determines that the value of the shortest distance is less than or equal to the predetermined threshold value, the image processing portion 22a determines that the current position of the distal end is a place that was passed through once, and performs processing so as not to display the insertion trail.

Further, the image processing portion 22a stores an image of the insertion trail, more specifically, position data (coordinate values) that were determined as not being places that were already passed through once in the trail image storage portion 61. When performing a re-examination, the image processing portion 22a reads out position data stored in the trail image storage portion 61 and displays the insertion trail that was stored at the time of the previous examination on the display apparatus 8.

Thus, even in a case where there is no three-dimensional data, the user can compare the insertion trail that was stored at the time of the previous examination and the insertion trail that is displayed at the time of the current examination, and observe the inside of the luminal organ in a manner such that there is no examination omission.

It is to be noted that with respect to each step in each flowchart of the present specification, the order of executing each step may be altered, steps may be executed simultaneously, or steps may be executed in a different order at each execution, as long as such execution is not contrary to the essential nature thereof.

The present invention is not limited to the above described embodiments, and various changes and alterations and the like can be made within a range that does not depart from the spirit and scope of the present invention.

What is claimed is:

1. An endoscope system, comprising:
    a storage portion that stores image information for constructing three-dimensional image information relating to a subject that is previously acquired;
    a luminal organ extraction portion that, by constructing the three-dimensional image information based on the image information, extracts a predetermined luminal organ that is present in the three-dimensional image information;
    an image pickup portion that picks up an image of inside the subject;
    a position information acquisition portion that acquires position information of the image pickup portion;
    a position alignment portion that makes the position information acquired by the position information acquisition portion correspond to position information of three-dimensional image coordinates of the predetermined luminal organ; and
    an image processing portion that generates trail information based on the position information of the image pickup portion, and based on a result of the position alignment portion, creates an image in which current distal end position information of the image pickup portion and determination information indicating a place that an image pickup portion distal end reaches inside the predetermined luminal organ and a place that the image pickup portion distal end has not reached, which are determined from the trail information, in different display forms are superimposed in a distinguishable manner on three-dimensional image information of the predetermined luminal organ.

2. The endoscope system according to claim 1, further comprising a determination portion that, based on a result of the position alignment portion, determines whether or not the image pickup portion passes through a duct in the predetermined luminal organ.

3. The endoscope system according to claim 2, wherein the determination portion determines whether or not the image pickup portion passes through based on distance information regarding a distance between a past position and a current position of the image pickup portion distal end.

4. The endoscope system according to claim 1, further comprising a virtual endoscopic image generation portion that generates a virtual endoscopic image in which the predetermined luminal organ is endoscopically seen from a predetermined observation point,
    wherein the image processing portion generates trail information based on the position information of the image pickup portion, and superimposes the trail information on the three-dimensional image information of the predetermined luminal organ, the virtual endoscopic image, or the image that is picked up by the image pickup portion, and displays the resulting image.

5. The endoscope system according to claim 1, wherein the image processing portion creates an image in which the determination information is superimposed in different colors.

6. The endoscope system according to claim 1, further comprising:
    an X-ray image acquisition portion that acquires X-ray information that is obtained by irradiating the subject with X-rays; and
    an extraction portion that extracts a predetermined structure from the X-ray information;
    wherein:
    the position alignment portion makes the predetermined structure correspond to the three-dimensional image information of the predetermined luminal organ; and
    the image processing portion superimposes the predetermined structure on the three-dimensional image information of the predetermined luminal organ and displays the resulting information.

7. The endoscope system according to claim 6, further comprising a determination portion that determines whether or not the image pickup portion passes through the predetermined structure based on a result of the position alignment portion,
    wherein if the determination portion determines that the image pickup portion passes through the predetermined structure, the image processing portion creates an image in which a display form of the predetermined structure is changed on the three-dimensional image information.

8. An endoscope system, comprising:
    a storage portion that stores image information for constructing three-dimensional image information relating to a subject that is previously acquired;
    a luminal organ extraction portion that, by constructing the three-dimensional image information based on the image information, extracts a predetermined luminal organ that is present in the three-dimensional image information;
    an image pickup portion that picks up an image of inside the subject;

a position information acquisition portion that acquires position information of the image pickup portion;

a position alignment portion that, makes the position information acquired by the position information acquisition portion correspond to position information of three-dimensional image coordinates of the predetermined luminal organ;

a determination portion that, based on a result of the position alignment portion, determines whether or not the image pickup portion passes through a duct in the predetermined luminal organ by setting a point that is nearest to centerline data of the predetermined luminal organ in the three-dimensional image information to be a trail point with respect to respective position coordinates of an image pickup portion distal end; and an image processing portion that, based on the result of the position alignment portion, generates trail information from the position information of the image pickup portion, and superimposes past trail information in the trail information on centerline data of a range in which the trail point exists, and creates an image in which insertion shape information including current distal end position information of the image pickup portion, and determination information which is obtained by determining whether or not the image pickup portion passes through a duct in the predetermined luminal organ are superimposed in a distinguishable manner on three-dimensional image information of the predetermined luminal organ.

\* \* \* \* \*